(12) United States Patent
Nakamura

(10) Patent No.: US 8,875,698 B2
(45) Date of Patent: Nov. 4, 2014

(54) GAS MIST INHALER

(75) Inventor: Shoichi Nakamura, Nagano (JP)

(73) Assignees: ACP Japan, Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 582 days.

(21) Appl. No.: 12/998,582

(22) PCT Filed: Feb. 26, 2010

(86) PCT No.: PCT/JP2010/053052
§ 371 (c)(1),
(2), (4) Date: Jun. 21, 2011

(87) PCT Pub. No.: WO2010/098430
PCT Pub. Date: Sep. 2, 2010

(65) Prior Publication Data
US 2011/0247610 A1 Oct. 13, 2011

(30) Foreign Application Priority Data

Feb. 26, 2009 (JP) .................. 2009-044125
Mar. 6, 2009 (JP) .................. 2009-053093

(51) Int. Cl.
*A61M 11/02* (2006.01)
*A61M 11/06* (2006.01)
*A61M 11/00* (2006.01)
*A61M 16/06* (2006.01)

(52) U.S. Cl.
CPC ............... *A61M 11/02* (2013.01); *A61M 11/06* (2013.01); *A61M 11/002* (2013.01); *A61M 11/003* (2013.01); *A61M 16/06* (2013.01); *A61M 16/0666* (2013.01); *A61M 2202/0208* (2013.01); *A61M 2205/8218* (2013.01)

USPC ............ 128/200.18; 128/200.14; 128/200.11

(58) Field of Classification Search
CPC ...... A61M 11/06; A61M 11/00; A61M 11/04; A61M 11/08; A61M 15/00; A61M 15/009; A61M 15/08; A61M 16/00; A61M 16/06; A61M 16/10; A61M 2011/00; A61M 2011/001; A61M 2011/006; A61M 2011/06; A61M 2011/04; A61M 2015/08; A61M 2015/00
USPC ............ 128/200.11–200.24, 203.12, 203.15, 128/203.16, 203.17, 203.26, 203.27, 128/204.18, 204.21, 205.11
See application file for complete search history.

(56) References Cited

U.S. PATENT DOCUMENTS

| | | | | |
|---|---|---|---|---|
| 3,713,440 A | * | 1/1973 | Nicholes | 128/205.12 |
| 3,796,216 A | * | 3/1974 | Schwarz | 128/205.13 |
| 4,100,235 A | * | 7/1978 | Thornwald | 261/142 |
| 4,392,490 A | * | 7/1983 | Mattingly et al. | 128/202.27 |

(Continued)

FOREIGN PATENT DOCUMENTS

| | | |
|---|---|---|
| JP | H10-211284 | 8/1998 |
| JP | 2008-220661 | 9/2008 |

*Primary Examiner* — Annette Dixon
(74) *Attorney, Agent, or Firm* — Manabu Kanesaka

(57) ABSTRACT

A gas mist inhaler includes a gas supply device for supplying a gas containing oxygen, carbon dioxide, or a mixed gas of oxygen and carbon dioxide, a gas mist generation device connected to the gas supply device for storing a liquid inside thereof and generating a gas mist prepared by pulverizing and dissolving the liquid stored in the gas mist generation device and the gas supplied from the gas supply device, and an inhalation member connected to the gas mist generation device and containing an inhalation port of inhaling the gas mist into a living organism.

19 Claims, 10 Drawing Sheets

(56) References Cited

U.S. PATENT DOCUMENTS

| | | | |
|---|---|---|---|
| 4,792,097 A * | 12/1988 | Kremer et al. | 239/338 |
| 4,886,055 A * | 12/1989 | Hoppough | 128/200.14 |
| 4,938,209 A * | 7/1990 | Fry | 128/200.21 |
| 5,020,530 A * | 6/1991 | Miller | 128/203.28 |
| 5,584,285 A * | 12/1996 | Salter et al. | 128/200.21 |
| 5,586,551 A * | 12/1996 | Hilliard | 128/203.29 |
| 6,131,568 A * | 10/2000 | Denyer et al. | 128/200.21 |
| 6,340,023 B2 * | 1/2002 | Elkins | 128/200.21 |
| 6,412,481 B1 * | 7/2002 | Bienvenu et al. | 128/200.21 |
| 6,609,515 B2 * | 8/2003 | Bienvenu et al. | 128/200.21 |
| 7,669,595 B1 * | 3/2010 | Mitchell | 128/203.12 |
| 7,836,884 B2 * | 11/2010 | Wright | 128/203.16 |
| 8,181,650 B2 * | 5/2012 | Nelson et al. | 128/205.17 |

* cited by examiner

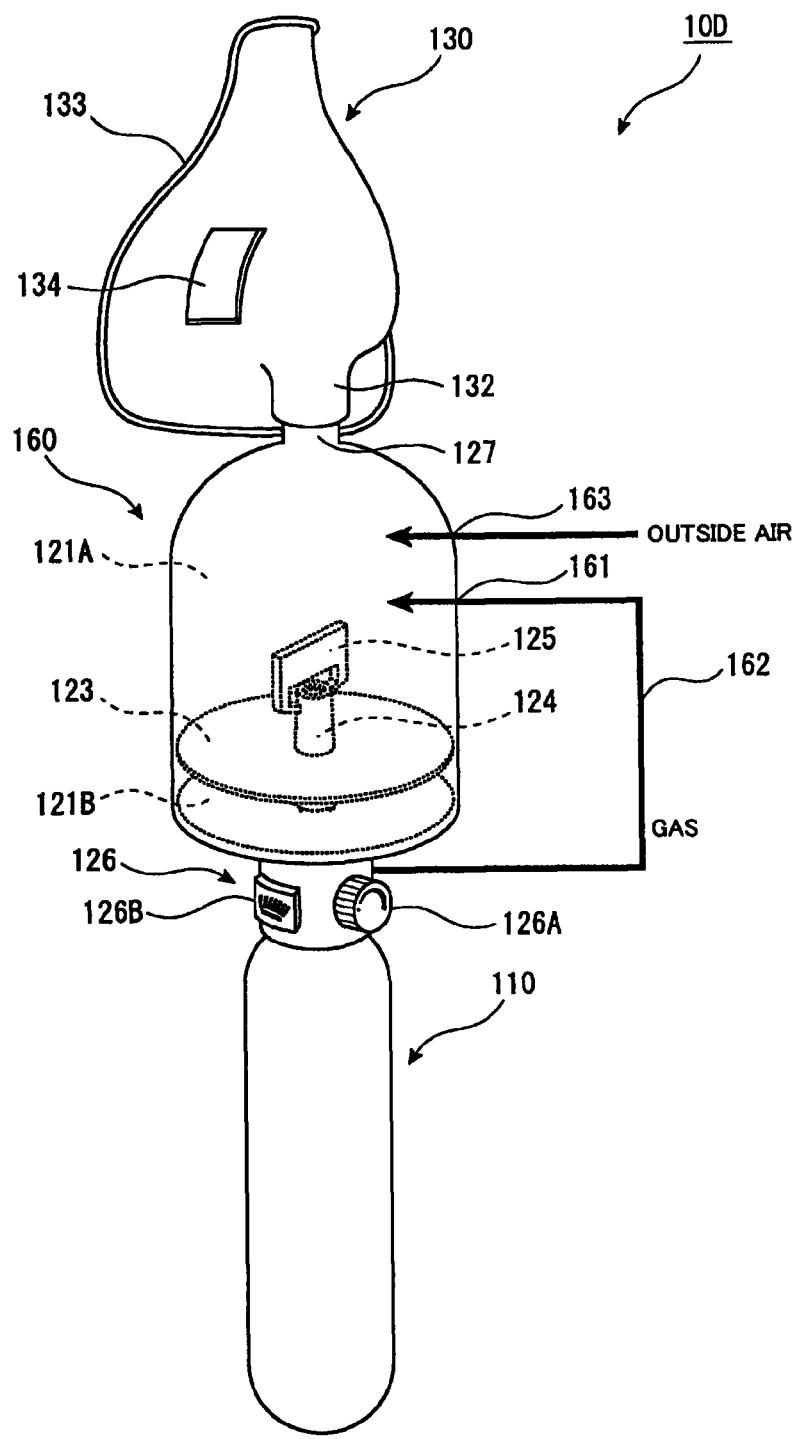

GAS MIST INHALER

RELATED APPLICATIONS

The present application is National Phase of International Application No. PCT/JP2010/053052 filed Feb. 26, 2010, and claims priorities from, Japanese Applications No. 2009-044125 filed Feb. 26, 2009 and No. 2009-053093 filed Mar. 6, 2009, the disclosure of which are hereby incorporated by reference herein in its entirety.

TECHNICAL FIELD

The present invention relates to a gas mist inhaler for carrying out oral inhalation of a gas mist into a living organism, which is prepared by pulverizing and dissolving oxygen, carbon dioxide, or a mixed gas of oxygen and carbon dioxide, and liquid.

BACKGROUND ART

It has conventionally been known that if carbon dioxide (carbonic acid anhydride: $CO_2$) contacts the skin and the mucous membrane of the living organism, it penetrates into them only thereby, and it expands blood vessels around the parts of penetrated carbon dioxide and works to improve the blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living organism works to release oxygen carried in combination with hemoglobin in a red blood cell. Around parts at the high density of carbon dioxide, the red blood cell releases more oxygen. Thus, supply of oxygen to cells by the red blood cell is mainly controlled by carbon dioxide. In short, being without carbon dioxide, hemoglobin remains as combined with oxygen, and the cell becomes unable to receive oxygen. As is seen, carbon dioxide seems to have been a waste product resulted from action of the cell, however, it plays in fact very important roles in the living-body.

Further, in recent times, oxygen of high density has also widely been known as effective in activity of metabolism, fatigue recovery or stability of blood pressure.

By the way, for easing a symptom of disease in a respiratory system such as asthma or allergic rhinitis, an inhaler has been till now used for oral inhalation of a medicine or steam. As the inhaler, a jet system (compressor) inhaler has broadly been employed which makes use of an air flow at high speed to make fine droplets based on a spraying principle.

SUMMARY OF INVENTION

Problems to be Solved by the Invention

The jet system (compressor) inhaler as mentioned above usually uses the flow at high speed of compressed air.

Accordingly, in view of the above circumstances, it is an object of the invention to provide a gas mist inhaler being simple and excellent in effects by using physiological actions of carbon dioxide or oxygen.

Means for Solving the Problem

For solving the above mentioned problems, the invention is to provide a gas mist inhaler having a gas supply means for supplying oxygen, carbon, or a mixed gas (called as "gas" hereafter) of oxygen and carbon dioxide, a gas mist generation means connected to the gas supply means for storing a liquid inside thereof and generating a mist (called as "gas mist" hereafter) prepared by pulverizing and dissolving the stored liquid and the gas, and an inhalation member connected to the gas mist generation means and having an inhalation port of inhaling the gas mist into the living organism, characterized by inhaling the gas mist into the upper airway and the lower airway of the living organism.

By the way, the invention refers it as "pulverizing and dissolving" to pulverize the liquid into fine liquid drops, and cause to contact and mix with gas (oxygen or carbon dioxide, or the mixed gas of oxygen and carbon dioxide).

Herein, the inhalation member preferably has an opening for taking in an outside air.

The gas supply means is desirably a gas bomb of a cartridge system. Otherwise, the gas supply means may has any one or in plurality of a gas supply time setting portion, a gas supply pressure adjusting portion and a gas mixing ratio setting portion.

In addition, the gas mist generation means also may supply the gas mist into a plurality of inhalation members.

It is optimum that the above mentioned liquid is any one or plural combination of water, ionic water, physiological salt solution, ozone water, purified water or sterilized and purified water. Desirably, this liquid further contains any one or plural combination of menthol, vitamin E, vitamin C derivative, retinol, anesthetic, cyclodextrin, photocatalyst, complex of photocatalyst and apatite, hyaluronic acid, coenzyme Q10, seed oil, propolith, ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate, high density carbonate spring, anti-allergic agent, anti-inflammatory agent, anti-febrile, anti-fungus agent, anti-influenza virus, influenza vaccines, steroid substance, carcinostatic substance, antihypertensive agent, cosmetic agent, or trichogen.

Sizes of the gas mist supplied from the gas mist generation means into the inhalation member are suitably smaller than 10 μm.

Further, the gas mist generation means is shaped in dome of convex having a curved face toward its upper portion and is provided with a gas mist discharge portion at the dome shaped top.

Desirably, the gas mist generation means has a gas mist supply pipe for supplying the gas mist into the inhalation member, and this gas mist supply pipe has a filter for removing liquid drops attached to a pipe inside. Further, a whole or one part of the gas mist supply pipe is suitably composed of a cornice shaped pipe, and this gas mist supply pipe is provided with a check valve.

Further, the gas mist generation means has a storage of storing the gas mist, and this storage is desirably placed with one or plurality of pored plates for refining the gas mist.

The gas mist generation means has the storage of storing the gas mist, and this storage may be structured to provide a gas supply port for directly supplying the gas from the gas supply means and an intake of taking in the outside air.

Preferably, the gas mist generation means has been in advance sterilized.

Advantageous Effects of the Invention

According to the gas mist inhaler of the invention, adding to ordinary effects of the inhaler, by the physiological action of the gas mist, not only permeating a liquid medicine into the upper and lower airways of the living organism, but also activating a blood flow around a diseased part, the invention can display effects such as flourishing the blood flow of the disease, rapidly moderating an inflammation or increasing immunological force.

BRIEF DESCRIPTION OF DRAWINGS

FIG. 10 A generally schematic view of the gas mist inhaler depending on a fourth embodiment of the invention.

DESCRIPTION OF EMBODIMENTS

In the following description, explanations will be made to embodiments of this invention, referring to the attached drawings.

First Embodiment

Figure 1:
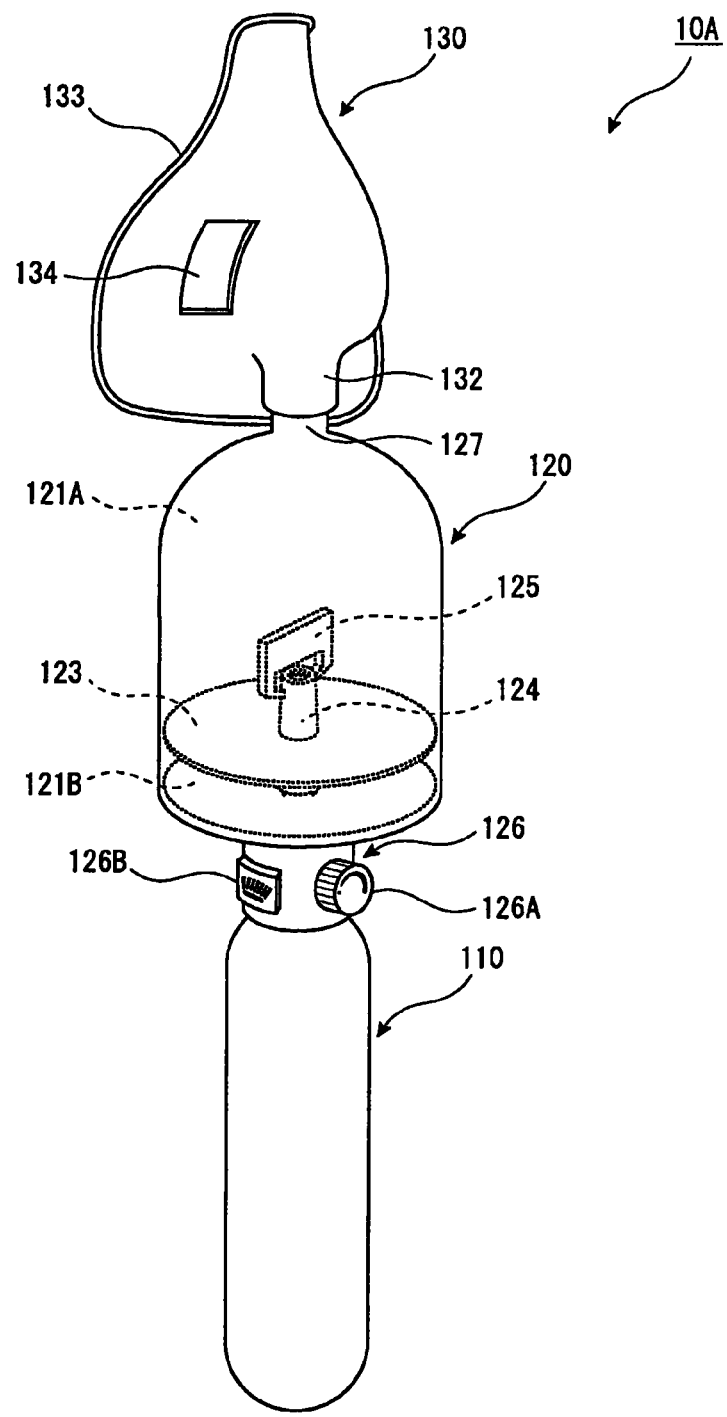
FIG. 1 A generally schematic view of the gas mist inhaler depending on a first embodiment of the invention.

FIG. 1 is the generally schematic view of the gas mist inhaler depending on the first embodiment of the invention. As shown in this Figure, the gas mist inhaler 10A of the present embodiment has the gas bomb 110 as the gas supply means, the gas mist generator 120 as the gas mist generation means and the inhalation mask 130 as the inhalation member.

With respect to the gas bomb 110 of supplying oxygen, carbon dioxide, or the mixed gas (called as "gas" hereafter) of oxygen and carbon dioxide, the present embodiment employs a small sized cartridge system, giving attention to portability. This small sized gas bomb 110 is, as shown in FIG. 1, attached to the gas bomb connecting portion 126 of the gas mist generator 120 and supplies the gas into the gas mist generator 120 at predetermined pressure.

Figure 2:
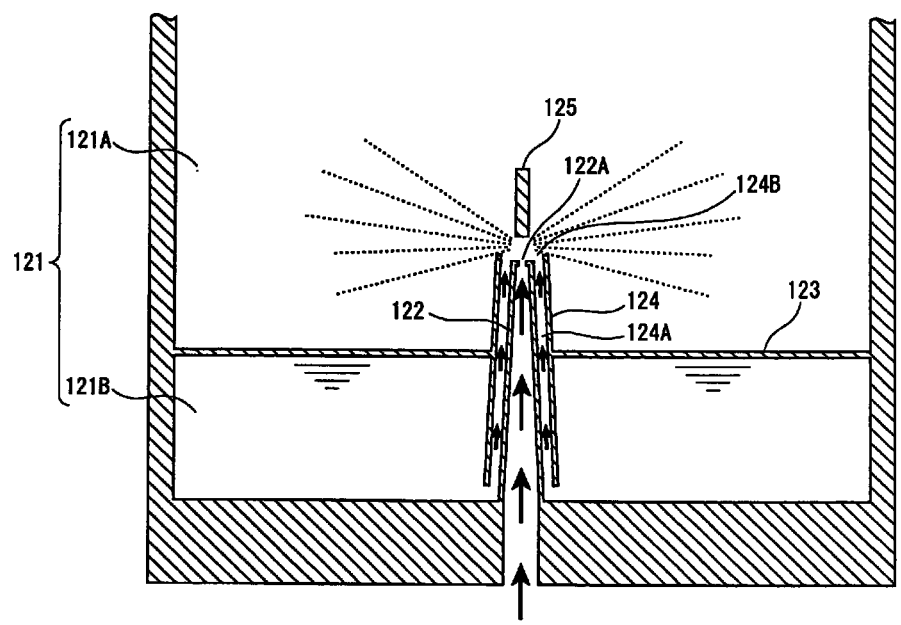
FIG. 2 A partially cross sectional view of the gas mist generator of FIG. 1.
Figure 3:
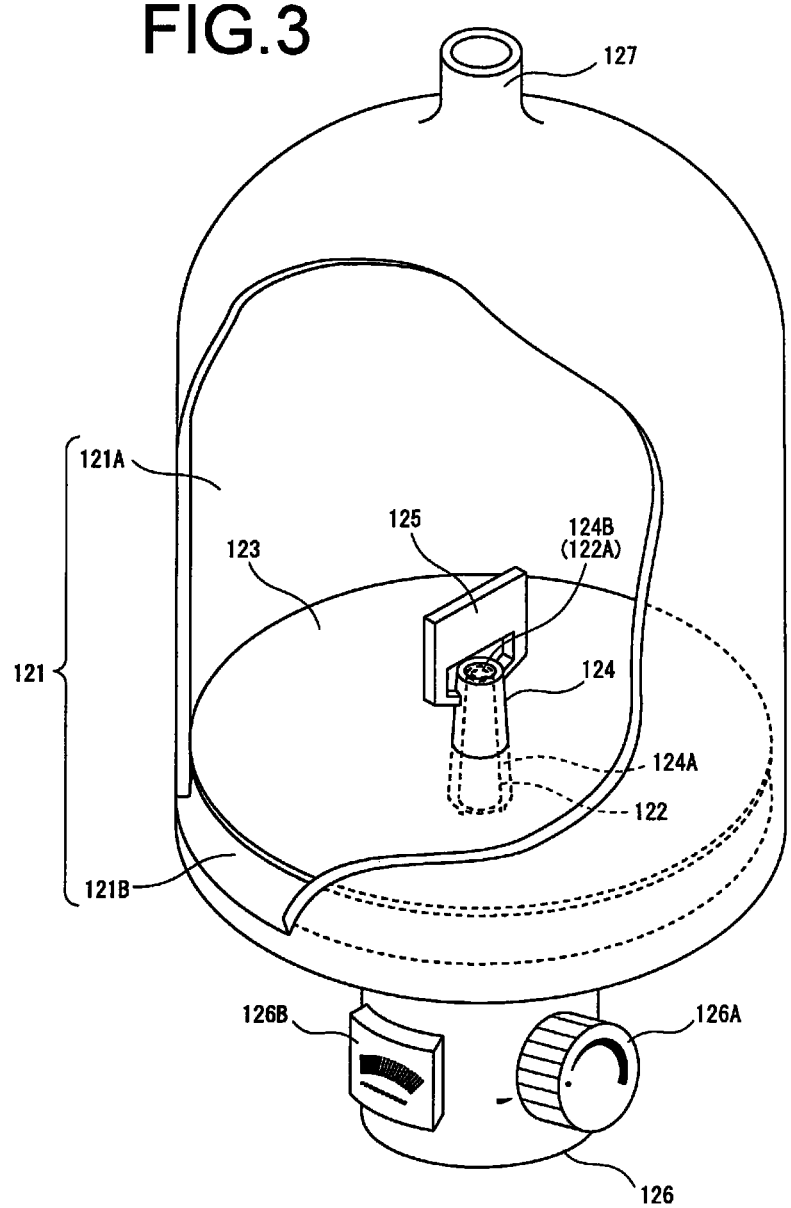
FIG. 3 A perspective view, partially in section, of the gas mist generator of FIG. 1.

The gas mist generator 120 stores inside a liquid, generates the gas mist by pulverizing and dissolving this liquid and the gas owing to high speed of the gas supplied from the gas bomb 110, and supplies it to the inhalation mask 130. In FIGS. 2 and 3, the structure of the gas mist generator 120 is illustrated. As seeing therein, the gas mist generator 120 is equipped with the storage 121 composed of the gas mist storage 121A storing the gas mist and a liquid storage 121B storing the liquid, a nozzle 122 discharging the gas supplied from the gas bomb 110 from a front end opening 122A, a liquid suction pipe forming member 124 defining a liquid suction pipe 124A sucking up the liquid stored in the liquid storage 121B until the front end of the nozzle 122, a baffle 125 positioned at a place opposite to the front end opening 122A, a gas bomb connecting portion 126 connected to the gas bomb 110, and a gas mist discharge port 127 discharging the generated gas mist.

The liquid (the liquid containing a later mentioned liquid medicine) stored in the liquid storage 121B is previously injected with a predetermined liquid medicine at a step of manufacturing the present gas mist generator 120 (in a case of a disposable type), otherwise in case of a type refilling to use the liquid (the liquid containing a later mentioned), a capped liquid refilling inlet (not shown) is provided at an upper part of the gas mist storage 121A of the gas mist generator 120, and a pipe or a tube is provided for refilling the liquid between the liquid refilling inlet and the liquid storage 121B.

The storage 121 is, as shown in FIG. 3, divided into the gas mist storage 121A and the liquid storage 121B by a shielding plate 123. The upper side (the side of the nozzle front end opening 122A) of the shielding plate 123 is the gas mist storage 121A storing the generated gas mist, while the lower side (the side of the gas bomb connecting portion 126) is the liquid storage 121B storing the liquid.

By the way, the shielding plate 123 serves to force up the liquid in the liquid suction pipe forming member 124 by maintaining pressure within the liquid storage 121B highly than pressure within the gas mist storage 121A. Therefore, the shielding plate 123 may be stationary at a predetermined position of an inner wall of the liquid storage 121B, or may be vertically movable in response to the level of a liquid surface within the liquid storage 121B. Further, depending on magnification of gas pressure issued from the front end opening 122A, the shielding plate 123 may be absent.

At the bottom center of the storage 121, a nozzle 122 is placed. The nozzle 122 communicates the bottom of the storage 121 and the gas bomb connecting portion 126, and is shaped to be almost circular cone toward an upper side from the bottom of the storage 121. The nozzle 122 is connected at its base end to the gas bomb connecting portion 126, to which the gas bomb 110 can be directly connected. The nozzle 122 projects at its front end to the side of the gas mist storage 121A, and can discharge the gas from the front end opening 122A.

The liquid suction pipe 124A is defined between the outer circumference of the nozzle 122 and the inner circumference of the liquid suction pipe forming member 124 of the almost circular cone being larger by a turn than the nozzle 122. That is, as shown in FIG. 2, by covering the liquid suction pipe forming member 124 of the nozzle 122, the liquid suction pipe 124A is defined between the outer circumference of the nozzle 122 and the inner circumference of the liquid suction pipe forming member 124. At this time, since a nail shaped projection (omitting illustration) is provided at a base end of the liquid suction pipe forming member 124, a space is formed at a base end of the liquid suction pipe forming member 124 and the bottom of the liquid storage 121B, so that the liquid stored in the liquid storage 121B is drawn up from this space by the liquid suction pipe 124A. In addition, the front end 124B of the liquid suction pipe forming member 124 opens nearly the front end opening 122A of the nozzle 122, and the liquid drawn up by the liquid suction pipe 124A collides against the gas flow discharged from the nozzle 122.

The baffle 125 is a member disposed at a position in opposition to the front end opening 122A of the nozzle 122 and the front end 124B of the liquid suction pipe forming member 124, and in the present embodiment, this is connected to the liquid suction pipe forming member 124. Otherwise, such a structure may be available which is connected to the shielding plate 123 and the inside of the storage 121 or the inside of the gas mist generator 120. The liquid suction pipe forming member 124 is connected to the shielding plate 123 at the nearly central portion in the vertical directions. The shielding plate 123 is also connected at its outer circumference to the inside of the storage 121. Thus, desirably, the gas mist generator 120 is formed integrally as a whole.

The gas bomb connecting portion 126 communicates the base end of the nozzle 122 and has inside a regulator. The gas bomb connecting portion 126 is preferably structured so that the gas bomb 110 can be connected by one touch. This embodiment shows an example of furnishing the gas bomb connecting portion 126 with a dial switch 126A and a residual gage 126B. The dial switch 126A can adjust on-off of the gas supply and flow rate by rotation. The residual gage 126B is shown with the gas remaining rate of the gas bomb 110.

The gas mist generated in the gas mist generator 120 is fed from the connecting portion 132 connected to the gas mist discharge port 127 into the inhalation mask 130.

Preferably, the gas mist generator 120 is in advance processed with a sterilizing treatment, and the liquid is previously stored in the liquid storage 121B. Or, the liquid storage 121B is formed with a pouring inlet for pouring the liquid into the liquid storage 121B from which the liquid is in advance poured. That is, for actually using the gas mist inhaler 10, preferably, the liquid is already stored in the gas mist generator 120. In this case, the gas mist generator 120 is desirably disposable for inhaling the gas mist hygienically and simply.

Figure 4:
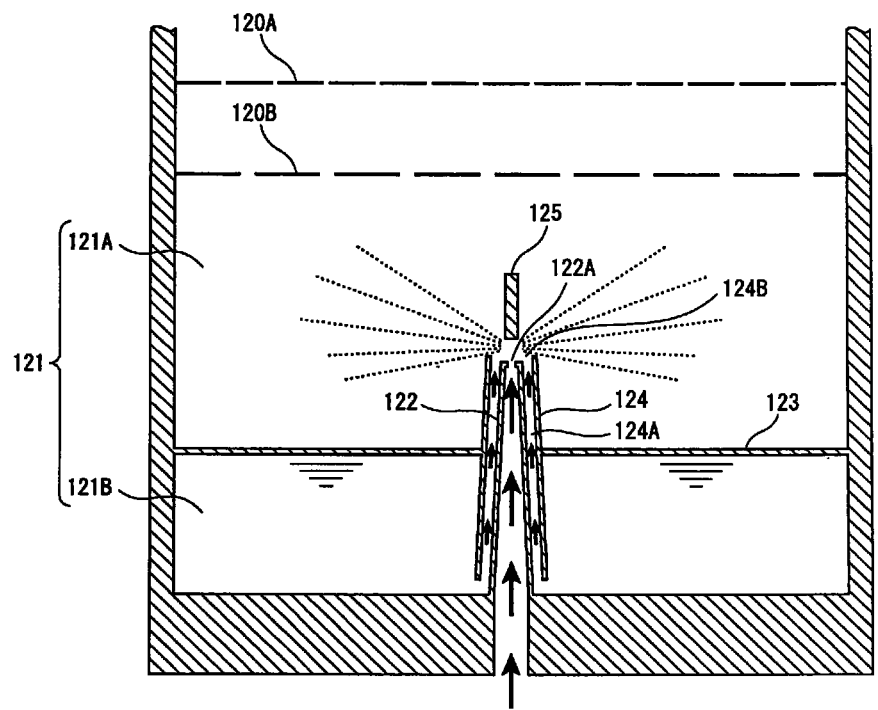
FIG. 4 A partially cross sectional view showing another example of the gas mist generator of the invention.
Figure 5A:
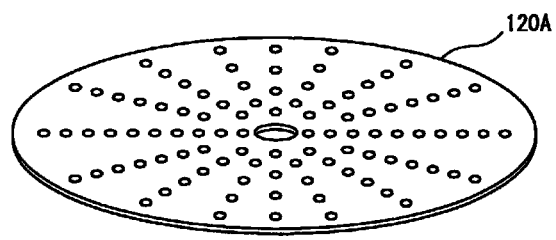
FIGS. 5A and 5B Perspective views showing examples of the plates to be placed within the gas mist generator of the invention.
Figure 5B:
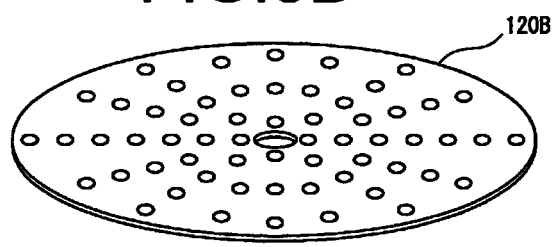

In addition, as shown in FIG. 4, at the position above the nozzle 122 of the gas mist storage 121A, one or plural sheets (in FIG. 4, two sheets as an example) of plates 120A, 120B may be furnished. FIGS. 5A and 5B show the examples of the plates 120A, 120B, respectively. Thus, the plates 120A, 120B are formed with plural pores, and the generated gas mist is refined when passing through the pores. With respect to the upper plate 120A and the lower plate 120B, it is preferable that the diameters of the pores of the upper plate 120A are smaller than those of the pores of the lower plate 120B.

Herein, for the liquid stored in the liquid storage 121B, it is preferable to employ water, ionic water, physiological salt solution, ozone water, purified water or sterilized and purified water. In addition, these liquids may contain medicines effective to users' diseases or symptoms. For the medicines, there are enumerated, for example, anti-allergic agent, anti-inflammatory agent, anti-febrile, anti-fungus agent, anti-influenza viral agent, influenza vaccines, steroid substance, carcinostatic substance, antihypertensive agent, cosmetic agent, or trichogen. Further, these liquids are mixed with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic moderating irritation to the mucous membrane; cyclodextrin removing odor; a complex of photocatalysis having disinfection and anti-phlogistic and apatite; hyaluronic acid having excellent water holding capacity and a skin moisture retention effect; coenzyme Q10 activating cells and heightening immunization; a seed oil containing anti-oxidation substance, or much nutrient; propolith having anti-oxidation function, anti-fungus function, ant-inflammatory function, pain-killing function, anesthetic function, and immunity function, and thus those substances are possible to generate synergistic effects by coupling with a gas physiological action. Otherwise, it is possible to add ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone iodine, sodium hydrogen carbonate. Further, it is also possible to add carbonate spring agent of high density of main components being carbonate and organic acid (as one example of effective components is sulfate, carbonate, organic acid, sodium dichloroisocyanurate).

The inhalation mask 130 is an inhalation member having a shape covering a user's inhaler (herein, the nose and mouth) for the user easily breathing the gas mist generated in the gas mist generator 120. The inhalation mask 130 is connected to the gas mist discharge port 127 of the gas mist generator 120 via the connecting portion 132, and the user breathes the gas mist from the inhalation port 133. The inhalation mask 130 is preferably formed with an opening 134 for taking in the outside air and avoiding evils by breathing oxygen of high density or carbon dioxide for along time.

Next, for breathing the gas mist with the gas mist inhaler 10A of the above mentioned first embodiment, at first, under a condition of already storing the liquid in the liquid storage 121B, the gas bomb 110 is set to the gas bomb connecting portion 126 of the gas mist generator 120. When turning a dial switch 126A of the gas bomb connecting portion 126, the gas starts to go into the nozzle 122. Further, the gas flowing rate is adjusted by the dial switch 126A. Since the nozzle 122 is reduced toward the front end as shown in FIG. 2, the gas from the gas bomb 110 increases the flowing speed and is discharged. The liquid is sucked up within the liquid suction pipe 124A owing to negative pressure caused by air flow at this time, and collides against the lower end of baffle 125. Desirably, the diameter of the mist generated by this collision is fine, and concretely, best is smaller than 10 μm. The thus finely pulverized mist can display effects of minus ion.

The generated gas mist spreads within the gas mist storage 121A and is discharged from the gas mist discharge port 127 following a convection of the gas. The gas mist storage 121A is desirably shaped in dome of convex having a curved face toward its upper portion as shown in FIG. 1. At the top portion of the dome shape, the gas mist discharge port 127 is formed. By making such a shape, it is possible to store more the gas mist, while avoiding that the mist contacts the upper portion of the interior wall of the gas mist storage 121A, goes back to the liquid and drops.

The gas mist discharged from the gas mist discharge port 127 is absorbed into the inhalation port 133 of the inhalation mask 130.

Figure 6A:
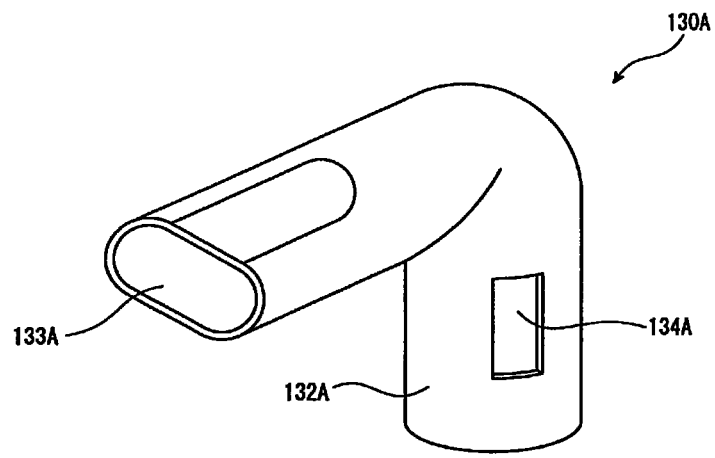
FIGS. 6A and 6B Perspective views showing modified examples of the inhalation members of the gas mist inhalers of the invention.
Figure 6B:
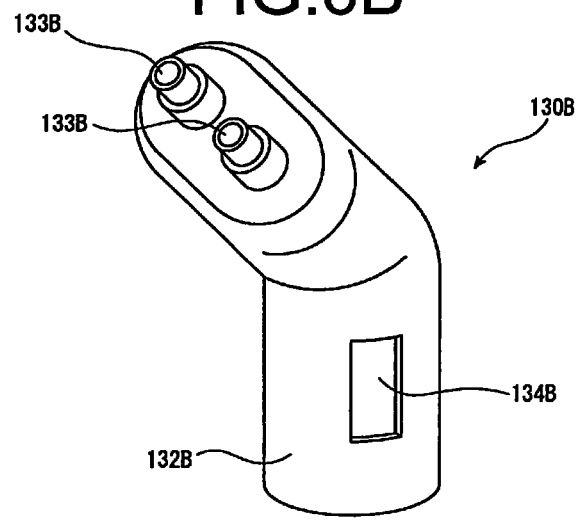

The above reference showed the example of using the inhalation mask 130 covering the nose and the mouth, and other various types using the inhalation members are available. FIGS. 6A and 6B show other examples of the inhalation members, respectively.

FIG. 6A is a mask 130A of a mouth piece type used for breathing from the mouth only. At the connecting portion 132A, it is connected to the gas mist discharge port 127 of the gas mist generator 120, and the user breathes the gas mist into the mouth from the inhalation port 133A. Also, the mouth mask 130A is desirably formed with the opening 134A for taking in the outside air. This mouth mask 130A is especially suitable to moderate symptoms of a throat.

FIG. 6B is a mask 130B of a nose piece type used for breathing from the nose only. At the connecting portion 132B, it is connected to the gas mist discharge port 127 of the gas mist generator 120, and the user breaths the gas mist into the nose from the inhalation port 133B. Also, the nose mask 130B is desirably formed with the opening 134B for taking in the outside air. This nose mask 130B is especially suitable to moderate allergic rhinitis of a throat.

Second Embodiment

The above first embodiment has shown the example as the gas supply means using the small sized gas bomb 110 of the cartridge system, and the present embodiment will show an example using a gas supply device of a stationary type.

Figure 7:
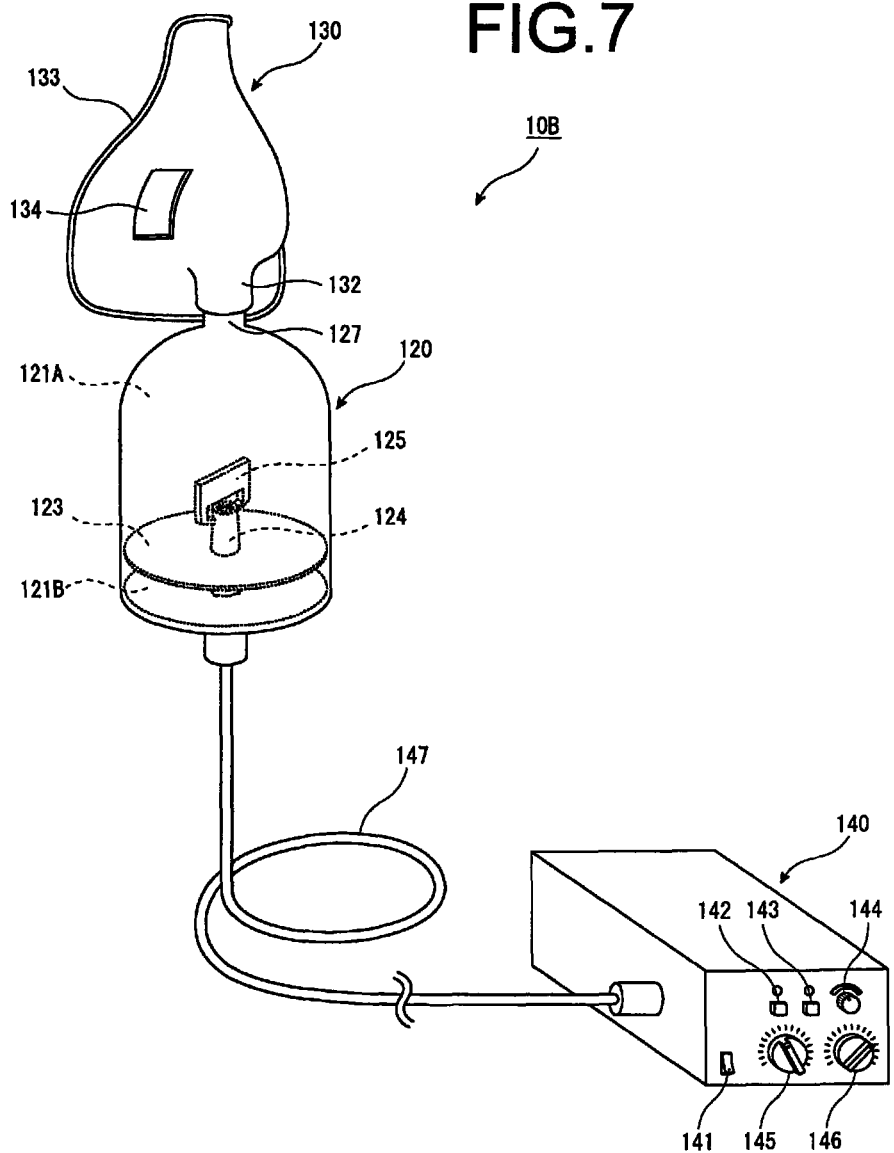
FIG. 7 A generally schematic view of the gas mist inhaler depending on a second embodiment of the invention.

FIG. 7 is the generally schematic view of the gas mist inhaler depending on the second embodiment of this invention. As to the same parts as those of the first embodiment shown in FIG. 1, the same numerals will be given, and detailed explanation will be omitted.

As shown in FIG. 7, the gas mist inhaler 10B has a gas supply device (gas supply means) 140, the gas mist generator (gas mist generating means) 120, and inhalation mask (inhalation member) 130.

The gas supply device 140 is a stationary typed gas supply device of the gas (oxygen, carbon dioxide or a mixed gas of oxygen and carbon dioxide) into the gas mist generator 120 at predetermined pressure. Its inside is built-in with the gas bomb (not shown), and may be built-in with a compressor, otherwise may be connected to an external gas bomb.

The gas supply device 140 is, for example as shown in FIG. 7, provided with a power switch 141, oxygen supply ON/OFF switch 142, carbon supply ON/OFF switch 143, gas mixing ratio setting portion 144, OFF timer (gas supply time setting portion) 145, and gas supply pressure adjusting portion 146. The gas supply device 140 and the gas mist generator 120 are connected via the gas supply pipe 147. The gas mixing ratio setting portion 144 is so composed as to regulate the mixing ratio of the carbon dioxide and the oxygen. It is thereby possible to reply at will to the user's requires, for example, for lightening asthma or recovering fatigue such as setting the mixing ratio of oxygen to be much, or for accelerating a blood circulation such as setting the mixing ration of carbon dioxide to be much. Further, the OFF timer 145 is for setting the gas supplying time, and when a set time passes away, the gas supplying is automatically stopped. The gas supply pressure adjusting portion 146 can set the gas supplying pressure arbitrarily. Since the gas supplying time or pressure are possible thereby, its using scope can be broadened.

Figure 8:
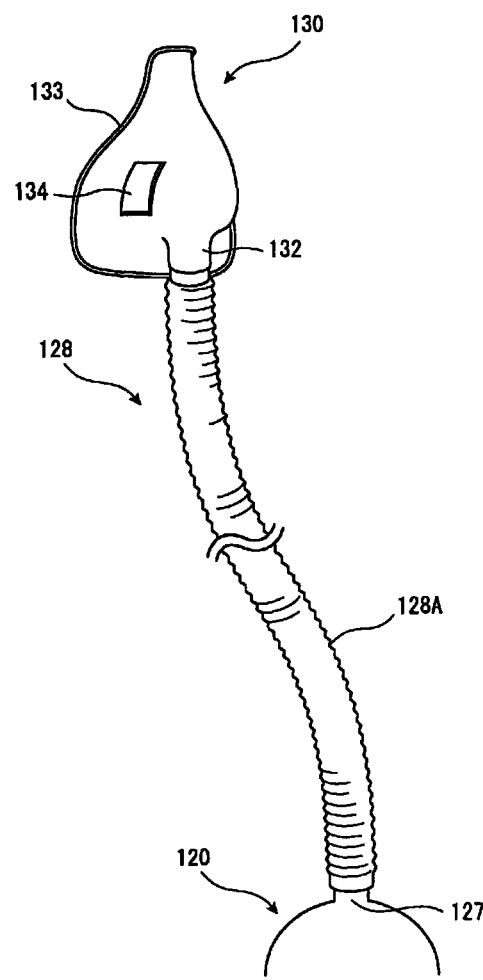
FIG. 8 A perspective view showing the example of the gas mist supply pipe connecting the gas mist generator to the inhalation member of the invention.

The above reference has shown the example where the gas mist discharge port 127 of the gas mist generator 120 is directly connected to the connecting portion 132 of the inhalation mask 130, and as shown in FIG. 8, the gas mist generator 120 may be connected to the inhalation mask 130 via the gas mist supply pipe 128. For such a case, the inside of the gas mist supply pipe 128 is furnished with a check valve for preventing back flow of the gas mist, though not illustrated. The gas mist supply pipe 128 may be provided with a filter for removing surplus liquid drops attached to a pipe inside, though not illustrated.

Further, if the gas mist supply pipe 128 is composed wholly or partially with a soft and cornice shaped pipe 128A of large diameter as shown in FIG. 8, it is freely bent or expanded and contracted so that the user's action is not limited. In addition, even if the gas mist flowing in the gas mist supply pipe 128 becomes liquefied, the cornice can remove the liquid owing to its concave and convex parts.

Third Embodiment

The above second embodiment has shown the example where one gas mist generator 120 is connected with one inhalation member 130, and the present embodiment will show a structure of connecting a plurality of inhalation members.

Figure 9:
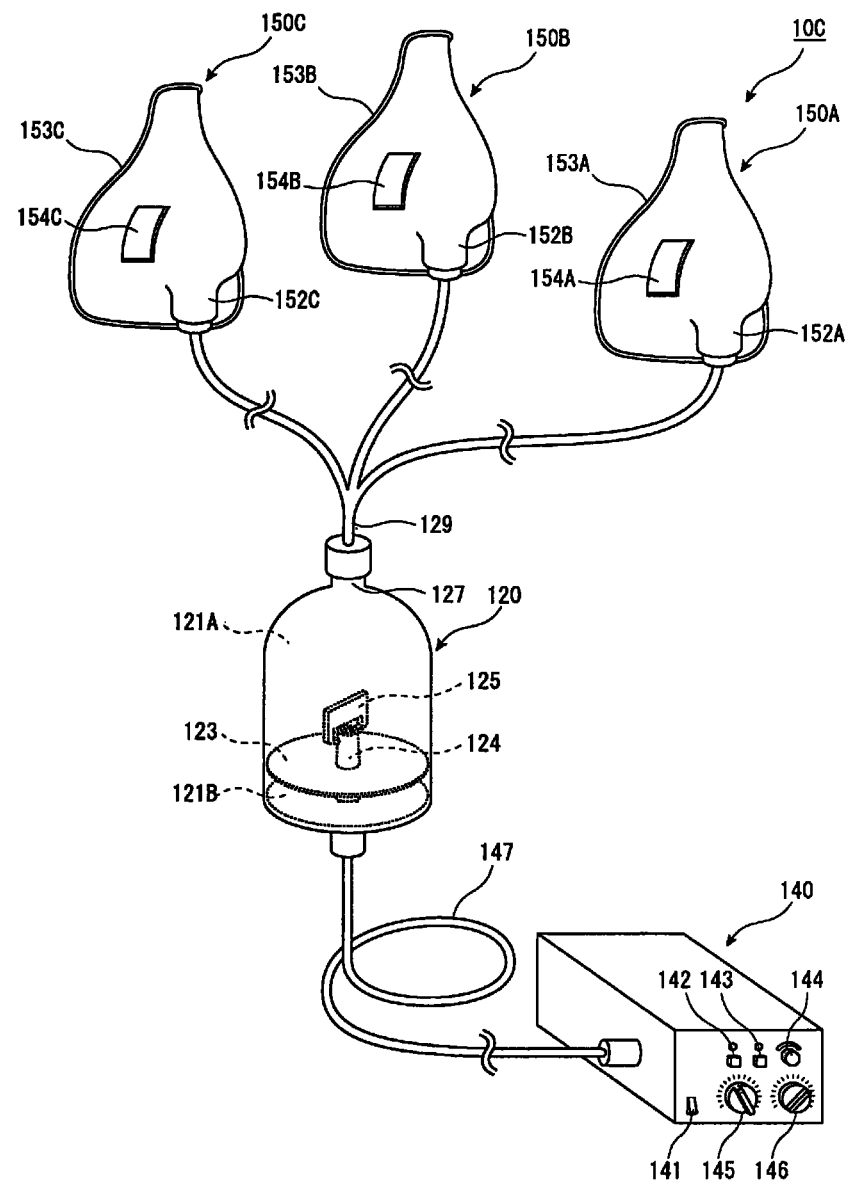
FIG. 9 A generally schematic view of the gas mist inhaler depending on a third embodiment of the invention.

FIG. 9 is the generally schematic view of the gas mist inhaler depending on the third embodiment of this invention. As to the same parts as those of the embodiment shown in FIGS. 1 to 8, the same numerals will be given, and detailed explanation will be omitted.

As shown in FIG. 9, the gas mist inhaler 10C has a gas supply device (gas supply means) 140, the gas mist generator (gas mist generating means) 120, and plural inhalation members (inhalation masks) 150. In the present embodiment, the plural inhalation members 150 includes inhalation members 150A, 150B, 150C, and the inhalation members 150A, 150B, 150C includes connecting portions 152A, 152B, 152C, inhalation ports 153A, 153B, 153C, and openings 154A, 154B, 154C, respectively.

The present embodiment equips gas mist supply pipe 129 diverging into a plurality (here, three) of pipes between the gas mist generator 120 and a plurality (here, three) of inhalation members 150A, 150B, 150C. It is thereby possible to connect the plurality (here, three) of inhalation members 150A, 150B, 150C to one gas supply device 140 and the gas mist generator 120. At this time, the gas supply device 140 adjusts the supplying pressure by the gas supply pressure adjusting portion 146 such that a gas inhalation can be performed optimally in each of the plural inhalation members 150A, 150B, 150C.

Herein, the gas mist supply pipe 129 may be inside provided with the check valve for preventing the back flow of the gas mist, though not illustrated. Further, the gas mist supply pipe 129 may be furnished inside with the filter for removing surplus liquid drops, though not illustrated. The gas mist supply pipe 129 may be composed wholly or partially with the soft and cornice shaped pipe of large diameter.

The present embodiment has illustrated the example using the gas mist supply pipes 129 diverging into the plurality of pipes, and may provide a plurality of gas mist discharge ports in the gas mist generator, or provide diverged plural pipes on the way of the gas mist pipes for supplying the gas mist into the plural inhalation members.

Fourth Embodiment

The above embodiment has the structure of supplying the gas from the nozzle 122 only into the gas mist generator 120 and taking in the outside air from the opening only of the inhalation member, but the present embodiment will refer to a structure having a gas supply port different from the nozzle in the gas mist generator.

FIG. 10 is the whole schematic view of the gas mist inhaler depending on the fourth embodiment of this invention. As to the same parts as those of the embodiment shown in FIGS. 1 to 9, the same numerals will be given, and detailed explanation will be omitted.

As shown in FIG. 10, the gas mist inhaler 10D of this embodiment has a gas bomb (gas supply means) 110, the gas mist generator (gas mist generating means) 160, and the inhalation mask (inhalation member) 130.

The gas mist generator 160 of this embodiment is provided with a gas supply port 161 and an outside air intake 163 communicating with the gas mist storage 121A and a gas supply pipe 162 connecting the gas supply port 161 from a gas bomb connecting portion 126.

The gas from the gas bomb 110 is supplied to the nozzle 122 within the gas mist generator 160 and at the same time also to the gas mist storage 121A from the gas supply port 161 via the gas supply pipe 162 from the gas bomb connecting portion 126. The gas supply port 161 or the gas supply pipe 162 are desirably furnished with a means (switch or the like) for starting or stopping the gas supply from the gas bomb 110.

The outside air intake 163 is preferably structured with an opening formed in the gas mist storage 121A. It is thereby possible to take in the outside air into the gas mist storage 121A and to avoid evils by breathing oxygen of high density or carbon dioxide for a long time. The outside air intake 163 is preferably structured with a means (open-close cover or the like) for starting or stopping the outside air.

The above reference has explained the example of applying the small sized gas bomb 110 of the cartridge system as the gas supply means, and also can apply to the gas supply device 140 of the stationary type. In such a case, the gas supply pipe may be directly connected to the gas supply device 140, or may be connected to the gas supply pipe 147 of the gas supply device 140.

As having above mentioned, according to the gas mist inhaler of the present invention, in addition to ordinary effects of the inhaler, owing to the physiological action of the gas mist, not only permeating the liquid medicine into the upper and lower airways of the living organism, also activating a blood flow around a diseased part, the invention can display effects such as rapidly moderating an inflammation or increasing immunological force.

The above reference has explained the embodiments of the invention, but is not limited to the above embodiments, and so far as not deviating from the subject matter of the invention, various kinds of embodiments are, of course, available.

INDUSTRIAL APPLICABILITY

The invention is concerned with the gas mist inhaler for carrying out the oral inhalation of the gas mist with industrial availability.

DESCRIPTION OF SYMBOLS

10A: gas mist inhaler
10B: gas mist inhaler
10C: gas mist inhaler
110: gas bomb
120: gas mist generator
120A: plate
120B: plate
121: storage
121A: gas mist storage
121B: liquid storage
122: nozzle
122A: front end opening
123: shielding plate
124: liquid suction pipe forming member
124A: liquid suction pipe
125: baffle
126: gas bomb connecting portion
126A: dial switch
126B: residual gage
127: gas mist discharge port
128: gas mist supply pipe
128A: cornice shaped pipe
129: gas mist supply pipe
130: inhalation mask
130A: mouth mask
130B: nose mask
132: connecting portion
132A: connecting portion
132B: connecting portion
133: inhalation port
133A: inhalation port
133B: inhalation port
134: opening
134A: opening
134B: opening
140: gas supply device
141: power switch
142: oxygen supply ON/OFF switch
143: carbon dioxide supply ON/OFF switch
144: gas mixing ration setting portion
145: OFF timer
146: gas supply pressure adjusting portion
147: gas supply pipe
150: plural inhalation members
150A: inhalation member
150B: inhalation member
150C: inhalation member
160: gas mist generator
161: gas supply port
162: gas supply pipe
163: outside air intake

The invention claimed is:

1. A gas mist inhaler comprising:
   a gas supply device for supplying a gas including oxygen, carbon dioxide, or a mixed gas of oxygen and carbon dioxide,
   a gas mist generation device connected to the gas supply device, for storing a liquid inside thereof and generating a gas mist prepared by pulverizing and dissolving the liquid stored in the gas mist generation device and the gas supplied from the gas supply device, and
   an inhalation member connected to the gas mist generation device and including an inhalation port of inhaling the gas mist into a living organism,
   wherein the gas mist generation device includes a storage, a shielding plate, a nozzle, a liquid suction pipe forming member and a baffle,
   the storage includes a gas mist storage for generating and storing the gas mist and a liquid storage for storing the liquid, and the shielding plate is arranged between the gas mist storage and the liquid storage to divide an inside of the storage into the gas mist storage and the liquid storage, the gas mist storage being positioned above the shielding plate and the liquid storage being positioned below the shielding plate,
   the nozzle communicates the gas supply device at the bottom of the storage, and the nozzle has a circular cone shape portion protruding into the gas mist storage through the liquid storage, and a front end opening positioned in the gas mist storage such that the gas supplied from the gas supply device flows to the gas mist storage,
   the liquid suction pipe forming member has a front end opening positioned in the gas mist storage and surrounds the nozzle with a space between an outer circumference of the nozzle and an inner circumference of the liquid suction pipe forming member, and the liquid suction pipe forming member is arranged to form a space between a base end of the liquid suction pipe forming member and a bottom of the liquid storage such that the liquid stored in the liquid storage is drawn up from the space between the base end of the liquid suction pipe forming member and the bottom of the liquid storage into the gas mist storage,
   the baffle includes a plate portion with two outer surfaces and one edge between the two outer surfaces, said one edge being positioned, in the gas mist storage, at a position facing the front end opening of the nozzle and the front end opening of the liquid suction pipe forming member, and is connected to the liquid suction pipe forming member, and the gas mist storage includes two pored plates for refining the gas mist, each having pores and being arranged above the baffle, and diameters of the pores of the pored plate in an upper side are smaller than those of the pores of the pored plate arranged at a lower side thereof.

2. A gas mist inhaler as set forth in claim 1, wherein the inhalation member has an opening for taking in an outside air.

3. A gas mist inhaler as set forth in claim 1, wherein the gas supply device is a gas bomb of a cartridge system.

4. A gas mist inhaler as set forth in claim 1, wherein the gas supply device has at least one of a gas supply time setting portion, a gas supply pressure adjusting portion and a gas mixing ratio setting portion.

5. A gas mist inhaler as set forth in claim 1, wherein the gas mist generation device supplies the gas mist into a plurality of inhalation members.

6. A gas mist inhaler as set forth in claim 1, wherein the liquid is at least one selected from the group consisting of water, ionic water, physiological salt solution, ozone water, purified water or sterilized and purified water.

7. A gas mist inhaler as set forth in claim 6, wherein the liquid further contains at least one selected from the group consisting of menthol, vitamin E, vitamin C derivative, retinol, anesthetic, cyclodextrin, photocatalyst, complex of photocatalyst and apatite, hyaluronic acid, coenzyme Q10, seed oil, propolith, ethanol, gluconic acid chlorohexizine, amphoteric surface active agent, benzalkonium chloride, alkyldiamino ether glycin acetate, sodium hypochlorite, acetyl hydroperoxide, sodium sesquicarbonate, silica, povidone-iodine, sodium hydrogen carbonate, high density carbonate spring, anti-allergic agent, anti-inflammatory agent, anti-febrile, anti-fungus agent, anti-influenza virus, influenza vaccines, steroid substance, carcinostatic substance, antihypertensive agent, cosmetic agent, or trichogen.

8. A gas mist inhaler as set forth in claim 1, wherein the gas mist supplied from the gas mist generation device into the inhalation member has sizes smaller than 10 μm.

9. A gas mist inhaler as set forth in claim 1, wherein the gas mist generation device is shaped in dome of convex having a curved face toward an upper portion thereof and is provided with a gas mist discharge portion at a top of the dome.

10. A gas mist inhaler as set forth in claim 1, wherein the gas mist generation device has a gas mist supply pipe for supplying the gas mist into the inhalation member, and the gas mist supply pipe has a filter for removing liquid drops attached to a pipe inside.

11. A gas mist inhaler as set forth in claim 1, wherein the gas mist generation device has a gas mist supply pipe for supplying the gas mist into the inhalation member, and at least one part of the gas mist supply pipe is composed of a cornice shaped pipe.

12. A gas mist inhaler as set forth in claim 1, wherein the gas mist generation device has a gas mist supply pipe for supplying the gas mist into the inhalation member, and the gas mist supply pipe is provided with a check valve.

13. A gas mist inhaler as set forth in claim 1, wherein the gas mist storage is structured to provide a gas supply port for directly supplying the gas from the gas supply device.

14. A gas mist inhaler as set forth in claim 1, wherein the gas mist storage has an intake for taking in the outside air.

15. A gas mist inhaler as set forth in claim 1, wherein the gas mist generation is sterilized in advance.

16. A gas mist inhaler as set forth in claim 1, wherein the shielding plate is vertically movable in response to a level of a liquid surface within the liquid storage.

17. A gas mist inhaler as set forth in claim 1, wherein the baffle includes two arm portions extending downwardly from two side portions of the plate portion and connected to the liquid suction pipe forming member.

18. A gas mist inhaler as set forth in claim 1, wherein the inhalation member includes a pipe portion connecting the gas mist generation device, an inhalation port arranged at one end portion of the pipe portion, and an opening arranged on the pipe portion; and the gas mist from the gas mist generation device is inhaled from the inhalation port into a living organism, and the opening takes in outside air.

19. A gas mist inhaler as set for the in claim 1, wherein the two pored plates are vertically spaced apart from each other.

* * * * *